United States Patent [19]

Harris

[11] Patent Number: 5,072,008
[45] Date of Patent: Dec. 10, 1991

[54] MANUFACTURE OF LACTOL DERIVATIVES

[75] Inventor: Gregory D. Harris, Wilmington, Del.

[73] Assignee: Imperial Chemical Industries PLC, London, England

[21] Appl. No.: 365,699

[22] Filed: Jun. 14, 1989

[30] Foreign Application Priority Data

Jun. 16, 1988 [GB] United Kingdom ............... 8814340

[51] Int. Cl.$^5$ ............................................. C07D 307/20
[52] U.S. Cl. ...................................... 549/475; 549/322; 549/375; 568/435; 562/470
[58] Field of Search ........................ 549/475; 568/435

[56] References Cited

U.S. PATENT DOCUMENTS 4,175,089  11/1979  Heiba et al. ...................... 260/343.6
4,723,037  2/1988  Harris ................................ 549/375

FOREIGN PATENT DOCUMENTS 0142323  5/1985  European Pat. Off. .
0201351  11/1986  European Pat. Off. .
0201354  11/1986  European Pat. Off. .
0202086  11/1986  European Pat. Off. .

OTHER PUBLICATIONS

Takeda, Bull. Chem. Soc. Jap. 41(6) 1468–71 (1968).
Pohmakotr et al., Chem. Lett., pp. 687–690, 1982.
Pohmakotr et al., Chemical Abstracts, vol. 97, p. 592, 1982, 109800q.
Takeda, Chemical Abstracts, vol. 69, p. 9932, 1968 106156V.
Peterson et al., Chemical Abstracts, 110(18): 163940K.
Fieser et al., Reagents for Organic Synthesis, vol. 5, p. 225.

Primary Examiner—Richard L. Raymond
Attorney, Agent, or Firm—Cushman, Darby & Cushman

[57] ABSTRACT

The invention concerns a novel process for the stereospecific manufacture of novel hydroxymethyl lactols of the formula I by a one step reduction of a corresponding lactone carboxylic ester of the formula II (many of which esters are novel) using a reducing agent such as diisobutylaluminium hydride at about ambient temperature. The lactols of formula I are intermediates for the production of pharmacologically active 1,3-dioxane alkenoic acids useful in the treatment of certain cardiovascular and pulmonary medical conditions. Certain of the esters of formula II are novel and are also included in the invention.

7 Claims, No Drawings

MANUFACTURE OF LACTOL DERIVATIVES

This invention concerns a novel process for the manufacture of hydroxymethyl lactol derivatives by the reduction of a lactone carboxylic ester. The hydroxymethyl lactol derivatives are useful in particular as intermediates for the production of 4-phenyl-1,3-dioxane alkenoic acids which themselves have utility as pharmaceuticals, for example in the treatment of certain pulmonary and/or cardiovascular medical conditions, by virtue of their ability to antagonise one or more of the actions of thromboxane $A_2$.

Various 4-phenyl-1,3-dioxane alkenoic acids are described, together with their pharmacological actions and medical applications, in a number of our earlier European patent publications, such as European patent no. 94239 and European patent applications, publication numbers 201351 and 201354. An improved process for the manufacture of the 4-phenyl-1,3-dioxane alkenoic acids from certain hydroxymethyl lactols and, more particularly, [2,3-trans]-tetra-hydro-2-phenyl-5-hydroxy-3-hydroxymethylfurans has also been described in our European patent application, publication number 142323. This patent application concerns, inter alia, the production of [2,3-trans]-tetrahydro-2-phenyl-5-hydroxy-3-hydroxymethylfurans using a two reagent step reduction of a lactone carboxylic acid, via an intermediate hydroxymethyl lactone. We have now discovered, and this is a basis for our present invention, that it is possible to obtain the [2,3-trans]-tetrahydro-2-phenyl-5-hydroxy-3-hydroxymethylfurans in high yields by a single reagent step reduction from a lactone carboxylic ester.

According to the invention there is provided a process for the manufacture of a [2,3-trans]-tetrahydro-2-phenyl-5-hydroxy-3-hydroxymethylfuran of the formula I, (or the open chain aldehyde form of formula Ia, or the isomer of formula Ib) [chemical formulae set out hereinafter] wherein benzene ring B may optionally bear one or two substituents selected from halogeno, (1–6C)alkyl, (1–6C)alkoxy, hydroxy, trifluoromethyl and nitro, which is characterised by selectively reducing a [2,3-trans]-tetrahydro-2-phenyl-5-oxo-3-furan-carboxylic acid ester of the formula II wherein benzene ring B has any of the meanings defined above and R is (1–8C)alkyl, phenyl, phenyl(1–4C)alkyl or phenoxy(1–4C)alkyl, in any of which the phenyl moiety is unsubstituted or bears a (1–4C)alkyl, (1–4C)alkoxy or halogeno substituent, with a branched chain alkyl aluminium hydride reducing agent, such as diisobutylaluminium hydride.

Particularly suitable values for substituents on ring B include, by way of example: for (1–6C)alkyl, methyl ethyl, isopropyl and butyl; for (1–6C)alkoxy, methoxy, ethoxy, propoxy and butoxy; and for halogeno, fluoro, chloro and bromo. A preferred value for ring B is, for example when it is unsubstituted or especially when it bears a 2-(1–4C)alkoxy (for example methoxy) substituent.

Particularly suitable values for R include, by way of example: for (1–8C)alkyl, methyl, ethyl, propyl, butyl, isobutyl, t-butyl, hexyl and octyl; for optionally substituted phenyl, unsubstituted phenyl, methylphenyl, methoxyphenyl, chlorophenyl and nitrophenyl; and for optionally substituted phenyl(1–4C)alkyl and phenoxy(2–4C)alkyl, benzyl, 1-phenylethyl, 2-phenylethyl and 2 phenoxyethyl, any of which may bear on the phenyl moiety an optional substituent selected from fluoro, chloro, methyl, ethyl, methoxy and ethoxy.

Preferred values for R include, for example, (1–6C)alkyl (such as methyl, ethyl, butyl and t-butyl), benzyl and 2-phenoxyethyl, of which ethyl and benzyl are particularly preferred.

Suitable hydride reducing agents include, for example, diisoamylaluminium hydride and diisobutylaluminium hydride, but the latter is particularly preferred.

The process of the invention is generally carried out in the presence of a suitable solvent or diluent, for example, a hydrocarbon solvent such as benzene, toluene, xylene, hexane (including mixtures of isomeric hexanes), a halogenated hydrocarbon solvent such as dichloromethane, or an ether solvent such as t-butyl methyl ether or 1,2-dimethoxyethane. A mixture of one or more such solvents and/or diluents may also be used. Particularly preferred solvents include, for example, toluene, dichloromethane, hexane and cyclohexane. The process of the invention is conveniently performed at a temperature in the range, for example, $-10°$ to $70°$ C. and more particularly in the range $0°$ to $60°$ C., and preferably in the range $0°$ to $30°$ C., such as at or near ambient temperature. The convenience for large scale manufacture of operating the process of the invention within the latter temperature range will be readily apparent to those skilled in the art of organic chemical processes.

It will be appreciated that the lactols of formula I may exist as a single epimer or mixture of both epimers of the 5-hydroxy group. In addition, the lactols of formula I can equilibrate (especially when in solution in polar solvents such as methanol and water) with the corresponding isomeric open chain aldehydes of the formula Ia and also the isomeric lactols of the formula Ib, which latter may also exist as a single epimer or mixture of both epimers of the lactol hydroxy group. The predisposition towards one isomer or another and the epimeric composition may vary with the particular value of benzene ring B or, in solution, with the nature of the solvent. However, it is believed that, for example, the o-methoxyphenyl compound described in Example 1 hereinafter exists in the crystalline state in the isomeric form of formula I and predominantly as a single epimer.

Nevertheless, by virtue of their ability to equilibrate with the open chain aldehydes of the formula Ia, either of the isomeric forms (that is that shown in formula I or Ib) is equivalent when used as a chemical intermediate, for example, when reacted with an ylid of the formula $(Ra)_3.P=CH.Y.CO_2M$ in which Ra is phenyl, methyl or ethyl, Y is polymethylene of 2 to 5 carbon atoms, optionally bearing a (1–4C)alkyl substituent and M is an alkali metal atom, to give a known erythro-diol of the formula III (as described previously in, for example, European patent application, publication no. 142323). Preferably Ra is phenyl, Y is ethylene or trimethylene and M is lithium, sodium or potassium. The reaction with the ylid is generally performed in a suitable diluent or solvent, for example, an aromatic solvent (such as benzene, toluene, xylene or chlorobenzene), an ether (such as t-butyl methyl ether, tetrahydrofuran or 1,2-dimethoxyethane), dimethyl sulphoxide or tetramethylene sulphone, or in a mixture of one or more such diluents and at a temperature conveniently in the range, for example, $15°-35°$ C.

The erythro-diols of the formula III are useful, for example, as chemical intermediates for conversion to the known 4-o-methoxyphenyl-1,3-dioxane-alkenoic acids of formula IV wherein Rb is, for example, trifluoromethyl, isopropyl, t-butyl, phenyl, chlorophenyl, cyanophenyl, 1-methyl-1-phenoxyethyl or 1-methyl-1-propoxymethyl and Y is, for example, ethylene or trimethylene, by reaction with a suitable aldehyde of the formula Rb.CHO (or an acetal or hemiacetal thereof) under generally acidic conditions, (as described previously in, for example, European patent 94239 and European patent applications, publication nos. 142323, 201351 and 201354). Particularly useful erythro-diols of the formula III, which are made readily accessible by the process of the invention, include, for example, erythro-4(Z)-8-hydroxy-7-hydroxymethyl-8-o-methoxyphenyl-4-octenoic acid [which is an intermediate to various 4(Z)-(1,3-dioxan-5-yl)hexenoic acids such as those of EPA 201351 and 201354] and erythro-5(Z)-9-hydroxy-8-hydroxymethyl-9-o-methoxyphenyl-5-octenoic acid [which is an intermediate to various 5(Z)-(1,3-dioxan-5-yl)heptenoic acids such as those exemplified in EP 94239]. Typical acidic conditions include, for example, hydrogen chloride, hydrogen bromide, sulphuric acid, phosphoric acid, p-toluenesulphonic acid and the anionic free acid form of a sulphonated polystyrene catalyst, and the converson is usually performed in a suitable solvent or diluent, such as diethyl ether, dibutyl ether, t-butyl methyl ether, 1,2-dimethoxyethane or tetrahydrofuran, at a temperature in the general range, for example, 10°–120° C., but conveniently, at or near ambient temperature.

The dioxanes of formula IV are precursors of the known, pharmaceutically useful, 4-o-hydroxyphenyl-1,3-dioxanes of the formula V, mentioned hereinbefore, and may be converted thereto by demethylation, for example, by reaction with sodium thioethoxide in a solvent such as N,N-dimethylformamide, at a temperature in the range, for example, 50°–160° C., or by reaction with diphenylphosphide in a suitable solvent, such as tetrahydrofuran or t-butyl methyl ether, at a temperature in the range, for example, 0°–60° C.

The invention also includes an improved multi-stage process for the production of compounds of the formula III, IV and also V characterised in that the lactol of formula I (or its isomer of formula Ib or the open chain aldehyde form of formula Ia) is produced by reduction of an ester of the formula II as stated hereinabove is used as the initial stage in the known multi-stage sequence.

Many of the esters of formula II are novel, for example those wherein ring B is alkoxy and R has any of the meanings defined hereinbefore and are provided as a further feature of the invention. The esters of formula II may be obtained by methods generally known for the production of structurally analogous compounds, which methods are included as a further aspect of the invention. Thus, they may be made by conventional esterification procedures including those illustrated in the accompanying Examples, for example (A): by reacting the corresponding acid of formula VI (also known as a "paraconic acid") with a suitable alkylating agent such as a sulphate of the formula R₂SO₄, for example an alkyl sulphate such as ethyl sulphate, in the presence of a suitable base, for example a tertiary amine such as triethylamine, conveniently in a suitable solvent or diluent, for example, a ketone (such as acetone, methyl ethyl ketone or isobutyl methyl ketone) or a hydrocarbon (such as benzene, toluene or xylene) and at a temperature in the range, for example, 30° to 80° C.

The esters of formula II may also be obtained, for example (B): by reacting the acid (or a reactive derivative thereof) with the appropriate hydroxy compound of the formula R.OH, conveniently in a suitable solvent or diluent (such as benzene, toluene, xylene, dichloromethane or t-butyl methyl ether, or in an excess of R.OH when it is a volatile alcohol), and at a temperature in the general range, for example, 0° to 60° C. When a reactive derivative of the acid of formula VI is used (such as the acid chloride which is particularly convenient), a suitable base, for example, a tertiary amine such as triethylamine is generally used and the reaction is carried out in then range 0° to 30° C. Suitable reactive derivatives include for example, the acid chloride, bromide, anhydride, mixed anhydride with formic acid, or the azide of the corresponding acid of formula V. These derivatives may be obtained by standard procedures of organic chemistry such as those illustrated hereinafter. When a free carboxylic acid is used, a dehydrating agent such as a carbodiimide is generally used and the reaction is performed at or about ambient temperature. The free acids of formula VI may also be esterified, for example using an excess of the alcohol of formula R.OH in the presence of an acid catalyst, for example, a mineral acid such as hydrogen chloride, sulphuric acid or p-toluenesulphonic acid, at a temperature in the general range, for example, 30° to 60° C. and in a suitable solvent or diluent such as is defined above.

Those esters of formula II in which R is an alpha-branched (3–8C)alkyl (such as t-butyl) may also be obtained, for example (C): by reacting an acid of the formula VI with the appropriate (3–8C)alkene (such as 2-methylpropene) in the presence of a strong acid such as hydrogen chloride or sulphuric acid, conveniently in a suitable solvent or diluent such as dichloromethane and a temperature in the general range, for example, 0° to 30° C.

The starting acids of formula VI may be obtained by conventional procedures of organic chemistry, for example as described in our European patent application, publication no. 142323.

It will be appreciated that the process of the invention is applicable to the production of optically active forms of the formula I compounds, for example, by use of an optically active form of the ester of formula II, itself obtained from an optically active form of an acid of formula VI. It will also be appreciated that in theory at least 3.0 molecular equivalents of hydride reducing agent should be required if complete reduction of both the ketone and carboxylic acid functional groups is to occur. However, in fact it is preferable to use about 2.5 to 2.8 (and, especially, about 2.6) molecular equivalents of the hydride reducing agent in the process for the production of the formula I compounds in order to minimise over-reduction to the corresponding triol of formula VII.

The production of the formula I compounds from the esters of formula II requires the full reduction of a carboxylic ester group to the corresponding hydroxymethyl and the selective reduction of a lactone to a lactol (as opposed to the corresponding open chain compound of formula VII). The present process surprisingly allows this to be carried out with a single hydride reducing agent (of which diisobutylaluminium hydride is preferred) in high yield and at reaction temperatures at or above ambient temperature making it particularly suitable for large scale manufacture.

The process of our earlier European patent application, publication number 142323, achieved the production of the compounds of formula I in two stages using first the toxic agent diborane and then diisobutylaluminium hydride, the latter generally at a temperature well below ambient temperature (typically at about −60° to −40° C.). The use of diborane on a large scale necessitates the use of special chemical plant to ensure that no reagent escapes. Equally, it is economically advantageous to avoid the necessity for carrying out chemical reactions at low temperatures, particularly below −10° C. since special stainless steel alloy reaction vessels are required instead of conventional glass or glass-lined vessels. Equally, whilst it is relatively straightforward to carry out reactions in the range −10° to +10° C. using conventional refrigeration equipment, more complex and expensive equipment is required to carry out chemical reactions on a large-scale below −10° C. Accordingly, the present invention overcomes a number of practical and economic probles associated with the previously described process for the production of compounds of formula I.

Certain of the esters of formula II are crystalline and are therefore especially useful as chemical intermediates, since they can be conveniently used and readily purified by recrystallisation. Such esters include the ethyl and benzyl esters described in the following Examples. These crystalline esters of formula II are provided as a still further feature of the invention.

The invention will now be illustrated in the following non-limiting Examples in which, unless stated otherwise:

(i) evaporations were carried out on a rotary evaporator in vacuo;
(ii) operations were carried out at room temperature, that is in the range 18° to 26° C.;
(iii) the progress of chemical reactions was assessed by thin layer chromatography (TLC) on 0.25 mm. Kieselgel 60F 254 plates (Art. 5715), available from E Merck, Darmstadt, W. Germany;
(iv) NMR spectra were determined at 270 MHz in $CDCl_3$ using tetramethyl-silane (TMS) as an internal standard and expressed as chemical shifts (delta values) in parts per million relative to TMS for major peaks, using the following abbreviations for designation of peaks: s, singlet; d, doublet; t, triplet; m, multiplet; br, broad;
(v) yields are provided for illustration and do not represent the maximum attainable by diligent development of the disclosed procedures; and
(vi) end-products were characterised by standard techniques of micro-analysis, infra-red, NMR and/or mass spectral analysis.

EXAMPLE 1

This example describes the production of [2,3-trans]-tetrahydro-5-hydroxy-3-hydroxymethyl-2-o-methoxyphenylfuran (B).

Ethyl [2,3-trans]-tetrahydro-2-o-methoxyphenyl-5-oxo-3-furancarboxylate (A) (see Example 7; 25 g; 0.095M) was slurried in dry toluene (50 ml) under an inert nitrogen atmosphere and cooled to 15° C. A 1.23M solution of diisobutylaluminum hydride in toluene (237 ml, 3 equivalents), was added slowly during one hour with rapid stirring, keeping the reaction temperature below 25° C. Butan-2-one (10 ml) was then added and the mixture was cooled to 10° C. It was then slowly added to a well-stirred mixture of butan-2-one (107 ml) and a solution of sodium potassium tartrate (120 g) in water (240 ml) at 60° C. This mixture was then stirred vigorously for one hour at 60° C. and then cooled to 40° C. The organic phase was separated and the solvent removed by distillation under atmospheric pressure. Toluene (190 ml) was added and the distillation continued to a head temperature of 108°–110° C. The residual material was cooled to 20° C. The crystalline solid which formed was collected by filtration, washed with toluene and dried at 60° C. to give [2,3-trans]-tetrahydro-5-hydroxy-3-hydroxy-methyl-2-o-methoxyphenylfuran (B) [17.0 g; 84% yield] as a white crystalline solid*, m.p. 110°–111° C. (mixture of C5 epimers) of high quality as judged by high pressure liquid chromatography (HPLC) and TLC.

* Essentially identical with that described in European patent application, publication no. 142323, Example 4.

EXAMPLE 2

This Example describes a general procedure for producing [2,3-trans]-tetrahydro-5-hydroxy-3-hydroxymethyl-2-o-methoxyphenyl-furan (B) by the process of the invention.

A solution of diisobutylaluminum hydride (3 molecular equivalents) in toluene is slowly added to a vigorously stirred suspension of ethyl [2,3-trans]-tetrahydro-2-o-methoxyphenyl-5-oxo-3-furancarboxylate (A) (1 part by weight) in dry toluene (2 parts by volume) under a nitrogen atmosphere and at a temperature of T° C., controlled as necessary by external cooling. When the reduction is complete, methyl ethyl ketone (butan-2-one, 0.2 parts by volume) is added. The reaction mixture is then added slowly to a mixture of butan-2-one (7 parts by volume) and sodium potassium tartrate (5 parts by weight) in water (10 parts by volume), keeping the temperature below 60° C. The mixture is then stirred at 60°–65° C. until all aluminum salts have dissolved. The phases are then separated at 60° C. The solvent is removed from the organic phase by distillation and the oily residue is dissolved in hot toluene (6 parts by volume) and then cooled to ambient temperature. The crystalline [2,3-trans]-tetra-hydro-5-hydroxy-3-hydroxymethyl-2-o-methoxyphenylfuran (B) is collected by filtration and dried at 50° C. to give material of melting point 110°–112° C.

EXAMPLE 3

This Example illustrates the effect of temperature on the process of the invention.

The reduction of ester A described in Example 2 was repeated using toluene as the solvent at various temperatures (T° C.) with the following results:

| T° C. | % Yield of furan B |
|---|---|
| 0 | 84 |
| 25 | 78 |
| 37 | 66 |
| 55 | 74 |
| 80 | 20 |

EXAMPLE 4

This Example illustrates the effect of solvent on the process of the invention.

The reduction of ester A described in Example 2 was repeated at a reaction temperature of 20°–25° C. (no external cooling) using solvent X in place of toluene and with the diisobutylaluminum hydride also dissolved in the same solvent X, with the following results:

| Solvent X | % Yield of furan B |
|---|---|
| dichloromethane | 78 |
| toluene | 78 |
| cyclohexane | 73 |
| hexanes (mixed isomers) | 67 |

EXAMPLE 5

This Example illustrates the use of different esters in place of the ethyl ester A.

The procedure described in Example 2 was repeated using the appropriate ester of the formula II (in which ring B is o-methoxyphenyl) in place of the ethyl ester A, using toluene as the solvent and carrying out the reaction at 20°–25° C., with the following results:

| R | % Yield of furan B |
|---|---|
| methyl | 71 |
| butyl | 78 |
| octyl | 48 |
| phenyl | 54 |
| benzyl | 79 |
| 2-phenylethyl** | 63 |
| 2-phenoxyethyl | 72 |
| p-nitrophenyl** | 51 |
| t-butyl | 72 |
| ethyl** | 85 |

[**using the (+)-optically active form of the ester and giving the (−) form of furan B, essentially identical with that described in European patent application, publication number 142323, Example 13(iii), i.e. m.p. 110–111° C., with [alpha]$_D$ −24.2° C. (methanol) at 25° C.]

EXAMPLE 6

This Example describes the preparation of a number of esters of the formula II for use in the process of the invention.

(a) A suspension of [2,3-trans]-tetrahydro-2-o-methoxyphenyl-5-oxo-3-furancarboxylic acid (C) (described in European patent application, publication number 142323) (32.9 g) in ethyl acetate (87 ml) and N,N-dimethylformamide (0.1 ml) was treated slowly with thionyl chloride (11.0 ml). The mixture was stirred at 35° C. for 2.5 hours. The clear yellow solution which formed was evaporated in vacuo to leave the acid chloride ([2,3-trans]-tetrahydro-3-chloroformyl-2-o-ethoxyphenyl-5-oxofuran) (D) as a dark coloured oil, which was used without further purification.

(b) The appropriate hydroxy compound R.OH (1.1 molecular equivalents) and triethylamine (1.1 molecular equivalents) were added to a solution of the acid chloride (D) (1.0 molecular equivalents) in toluene (3 parts by volume). The mixture was stirred at 0°–10° C. for 2 hours under an atmosphere of nitrogen. The solvent was removed by evaporation and the oily residue dissolved in diethyl ether. The ethereal solution was washed with water, then with saturated sodium hydrogen carbonate solution, dried (Na$_2$SO$_4$) and evaporated to give the ester of formula II. Solid esters were recrystallised from the appropriate solvent and any oily esters were characterised by NMR spectroscopy and were generally used without additional purification. Using the above procedure, the following esters of formula II were obtained:

| Ester Number | R | Optical Form | melting point (recrystallisation solvent) |
|---|---|---|---|
| 1 | ethyl | ± | 60–61° C. (cyclohexane) |
| 2 | phenyl | ± | 84–85° C. (2-propanol) |
| 3 | phenyl | + | 108–109° C. (2-propanol) |
| 4 | 2-phenylethyl | + | 69–70° C. (2-propanol) |
| 5 | 2-phenoxyethyl | ± | 71–72° C. (2-propanol) |
| 6 | p-nitrophenyl | + | 120–121° C. (2-propanol) |
| 7 | benzyl | ± | 81–82° C. (2-propanol) |
| 8 | methyl | ± | obtained as an oil |
| 9 | ethyl | + | obtained as an oil* |
| 10 | butyl | ± | obtained as an oil |
| 11 | octyl | ± | obtained as an oil |

[*[alpha]$_D$ + 30.8° (c = 1.0, ethanol)]

EXAMPLE 7

This Example describes the preparation of the ethyl ester of the acid C for use in the process of the invention.

Diethyl sulphate (53.8 g) and triethylamine (35.3 g) were added to a solution of the acid C (55.0 g) in isobutyl methyl ketone (250 ml). The mixture was stirred at 60° C. for 2 hours and then cooled to 20° C. washed with saturated sodium hydrogen carbonate (2×100 ml) followed by 10% w/w sodium chloride solution (5.0 ml). The organic phase was concentrated to about 90 ml in vacuo. Cyclohexane (188 ml) was then added. The solution was heated to 45° C. and then cooled with stirring to 5° C. over a period of 5 hours. The ethyl ester (A) of acid (C) crystallises out and is collected by filtration, washed with cyclohexane and dried at 40° C. to give material of m.p. 60° C.

EXAMPLE 8

This Example describes the preparation of the t-butyl ester of the acid C for use in the process of the invention.

2-Methylpropene (100 ml) and sulphuric acid (2.5 ml) were added to a suspension of the acid C (12.0 g) in dichloromethane (100 ml). The mixture was stirred for 48 hr at 25° C. during which time the solid dissolves. The reaction solution was added to a 20% w/v solution of potassium hydrogen carbonate in water (200 ml) and the organic phase was separated. The aqueous phase was extracted with diethyl ether (2×200 ml) and the combined organic extracts evaporated to give a clear yellow oil. Toluene (100 ml) was added and the solvent then removed by distillation under reduced pressure yielding the t-butyl ester (15.1 g) as an oil, of suitable purity for further use; NMR: 1.5 (9Hs), 2.8 (2H d), 3.4 (1H m), 3.8 (3H s), 5.8 (1H d), 6.7–7.4 (4H m).

EXAMPLE 9

This example describes the production of [2,3-trans]-tetra-hydro-5-hydroxy-3-hydroxymethyl-2-o-methoxyphenylfuran by reduction of ethyl [2,3-trans]-tetrahydro-2-o-methoxyphenyl-5-oxo-3-furancarboxylate.

The general procedure described in Example 2 is carried out with ethyl [2,3-trans]-tetrahydro-2-o-methoxyphenyl-5-oxo-3-furancarboxylate (1 molecular equivalent) but using 2.6 molecular equivalents of diisobutylaluminium hydride and a reaction temperature (T) of 15° to 20° C. There is thus obtained [2,3-trans]-tetra-hydro-5-hydroxy-3-hydroxymethyl-2-o-methoxyphenylfuran as a crystalline solid, essentially identical to that described in Examples 1 and 2, in a yield of 70–75%.

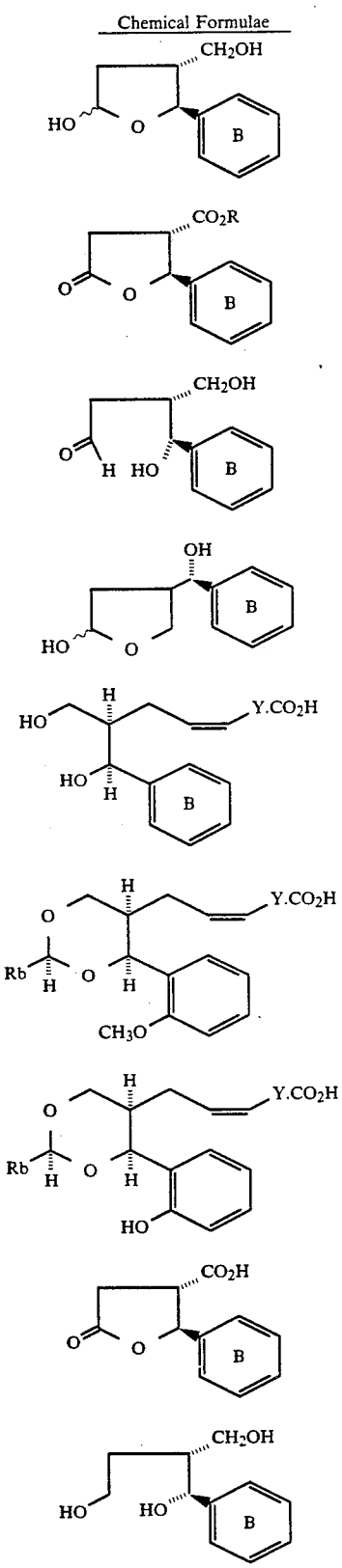

(or the open chain aldehyde form of formula Ia, or the isomer of formula Ib), wherein benzene ring B is unsubstituted or bears one or two substituents selected from the group consisting of halogeno, (1–6C)alkyl, (1–6C)alkoxy, hydroxy, trifluoromethyl and nitro, which process is characterised by selectively reducing a [2,3-trans]-tetrahydro-2-phenyl-5-oxo-3-furancarboxylic acid ester of the formula II wherein benzene ring B has any of the meanings defined above and R is (1–8C)alkyl, phenyl, phenyl(1–4C)alkyl or phenoxy(1–4C)alkyl, in any of which the phenyl moiety is unsubstituted or bears a (1–4C)alkyl, (1–4C)alkoxy or halogeno substituent, with a branched chain alkyl aluminium hydride reducing agent.

2. A process according to claim 1 which is characterised in that the reducing agent is selected from diisoamylbutylaluminium hydride and diisobutylaluminium hydride.

3. A process according to claim 1 or 2 characterised in that it is carried out in the presence of a suitable solvent or diluent selected from a hydrocarbon, halogenated hydrocarbon or an ether, or a mixture of one or more such solvents or diluents.

4. A process according to claim 3 characterised in that the solvent or diluent is selected from toluene, dichloromethane, hexane and cyclohexane.

5. A process according to claim 1 or 2 characterised in that the reduction is performed at a temperature in the range −10° to 70° C.

6. A process according to any one of claims 1 or 2 characterised in that about 2.5–2.8 molecular equivalents of the reducing agent are used.

7. A process for the manufacture of [2,3-trans]-tetrahydro-5-hydroxy-3-hydroxymethyl-2-o-methoxyphenylfuran (or the aldehyde form or isomer thereof, of formula Ia

What is claimed is:

1. A process for the manufacture of a [2,3-trans]-tetrahydro-2-phenyl-5-hydroxy-3-hydroxymethylfuran of the formula I, or Ib,

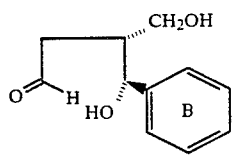
Ia

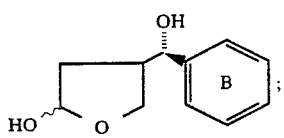
Ib respectively, in which benzene ring B is o-methoxyphenyl), which is characterised by reducing a [2,3-trans]-tetrahydro-2-phenyl-5-oxo-3-furancarboxylic acid ester of the formula II,

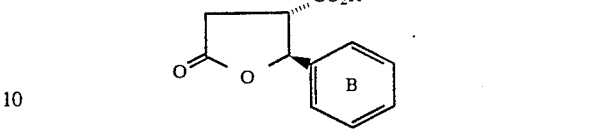

wherein benzene ring B is o-methoxyphenyl and R is selected from the group consisting of (1–6C)alkyl, benzyl and 2-phenoxyethyl, by reaction with about 2.6 molecular equivalents of diisobutylaluminium hydride, at a temperature in the range 0° to 30° C.

* * * * *